US009457148B2

(12) United States Patent
Holmqvist

(10) Patent No.: US 9,457,148 B2
(45) Date of Patent: Oct. 4, 2016

(54) MEDICAMENT DELIVERY DEVICE

(75) Inventor: Anders Holmqvist, Värmdö (SE)

(73) Assignee: SHL GROUP AB, Nacka Strand (SE)

( * ) Notice: Subject to any disclaimer, the term of this patent is extended or adjusted under 35 U.S.C. 154(b) by 393 days.

(21) Appl. No.: 13/262,633

(22) PCT Filed: Mar. 29, 2010

(86) PCT No.: PCT/EP2010/054073
§ 371 (c)(1),
(2), (4) Date: Nov. 4, 2011

(87) PCT Pub. No.: WO2010/115743
PCT Pub. Date: Oct. 14, 2010

(65) Prior Publication Data
US 2012/0172815 A1    Jul. 5, 2012

Related U.S. Application Data

(60) Provisional application No. 61/165,563, filed on Apr. 1, 2009.

(30) Foreign Application Priority Data

Apr. 1, 2009   (SE) ...................................... 0950208

(51) Int. Cl.
*A61M 5/20*   (2006.01)
*A61M 5/315*   (2006.01)

(52) U.S. Cl.
CPC ............ *A61M 5/20* (2013.01); *A61M 5/3158* (2013.01); *A61M 5/31555* (2013.01); *A61M 5/31578* (2013.01); *A61M 5/31536* (2013.01); *A61M 5/31558* (2013.01); *A61M 5/31575* (2013.01); *A61M 2005/3152* (2013.01)

(58) Field of Classification Search
CPC ......... A61M 5/31526; A61M 5/3153; A61M 5/31551; A61M 5/31555; A61M 5/3158; A61M 5/31585; A61M 5/31578; A61M 5/31536; A61M 5/31575; A61M 5/31583; A61M 5/31581; A61M 5/31576; A61M 5/3155; A61M 5/31548; A61M 5/31528; A61M 5/31525

USPC .................................................. 604/209, 224
See application file for complete search history.

(56) References Cited

U.S. PATENT DOCUMENTS

| 3,334,788 | A | * | 8/1967 | Hamilton | ........................ 222/43 |
| 2004/0210200 | A1 | * | 10/2004 | Gerondale | .......... A61M 5/3158 604/224 |
| 2005/0165363 | A1 | * | 7/2005 | Judson et al. | ................ 604/209 |
| 2007/0191784 | A1 | * | 8/2007 | Jacobs | .............. A61M 5/31555 604/224 |

FOREIGN PATENT DOCUMENTS

| WO | 2006128794 A2 | 12/2006 |
| WO | 2007063342 A1 | 6/2007 |
| WO | 2008101829 A1 | 8/2008 |

OTHER PUBLICATIONS

EPO, Intl Search Report in PCT/EP2010/054073, Sep. 17, 2010.
EPO, Written Opinion in PCT/EP2010/054073, Sep. 17, 2010.

* cited by examiner

*Primary Examiner* — Bhisma Mehta
*Assistant Examiner* — Laura Schell
(74) *Attorney, Agent, or Firm* — McDonnell Boehnen Hulbert & Berghoff LLP

(57) ABSTRACT

The present invention relates to a medicament delivery device comprising an elongated housing (10, 10') having opposite distal and proximal ends, a medicament container (18; 18') arranged inside said housing, a medicament delivery member (16; 16') attachable to said medicament container; a plunger rod (22; 22') arranged to act on a stopper (20; 20') inside said medicament container; driving means arranged to interact with said plunger rod; wherein said device further comprises an operation member (38; 38') transversally protruding through an elongated opening (39; 39') on the longitudinal surface of the elongated housing and interactively connected to the driving means for both setting and actuating the delivery of a dose of medicament.

7 Claims, 15 Drawing Sheets

MEDICAMENT DELIVERY DEVICE

The present application is a U.S. National Phase Application pursuant to 35 U.S.C. §371 of International Application No. PCT/EP10/54073 filed Mar. 29, 2010, which claims priority to U.S. Provisional Patent Application No. 61/165,563 filed on Apr. 1, 2009.

TECHNICAL AREA

The present invention relates to a medicament delivery device and in particular a medicament delivery device capable of delivering a number of doses of medicament.

TECHNICAL BACKGROUND

There are a number of medicament delivery devices on the market by which a user may set a dose of medicament to be delivered. Also many devices are capable of delivering a number of doses from a medicament container until it becomes empty. In this respect, each dose could have the same size, i.e. a fixed dose size or each dose could be individually set before delivery.

The majority of the devices developed for this purpose are provided with dose setting knobs, often placed in the distal end of the devices and intended to be turned or rotated in order to set a dose to be delivered. However, a turning motion is not always the optimum for some users, such as for example with reduced dexterity. It might then be difficult to actually set the desired and prescribed dose if the precision in the hands are gravely reduced due to e.g. rheumatism. Also, the turning motion is widely used because of the design of many delivery devices having generally tubular shapes and rotating components.

Another drawback with some known delivery devices is that it may require considerable force from the user for performing certain operations such as cocking or arming a device and/or subsequent injection.

One solution to the latter drawback is disclosed in US 2005/0165363. Here a manually operable piston, which is used for performing an injection, is operably connected to a drive member, which acts on a stopper in a medicament container for expelling medicament through a medicament delivery member, such as an injection needle. In order to facilitate the operation of the device also for users having reduced strength a gear set is arranged between the piston and the drive member, which gear set then reduces the force required for the operation. However there is no possibility of setting a dose.

There are several other documents disclosing different types of force reducing transmissions comprising toothed racks and cog-wheels, such as U.S. Pat. No. 5,782,633, WO 03/080160, WO96/26754 and WO 2008/058666. however, none of these documents disclose a transmission or function wherein the handling of a dose setting member or actuation member for setting a prescribed dose a certain distance, linear or rotational provides a linear or rotational distance that a dose providing member is moved, such as a driver acting on a plunger rod. This has proved a drawback, especially when rather small doses of medicament are to be set, whereby the accuracy of the dose setting distance cannot be guaranteed. It would be an advantage if the accuracy could be enhanced with this type of movement transmissions utilizing toothed racks and cog-wheels.

BRIEF DESCRIPTION OF THE INVENTION

A main aim of the present invention is to remedy the drawbacks of the medical delivery devices of the state of the art and in particular to provide a medical delivery device that is capable of providing the user with a novel and intuitive dose setting operation.

This aim is obtained by the features of the independent patent claim. Preferable embodiments of the invention form the subject of the dependent patent claims.

According to a main aspect of the present invention it is characterised by a medicament delivery device comprising an elongated housing having opposite distal and proximal ends, a medicament container arranged inside said housing, a medicament delivery member attachable to said medicament container; a plunger rod arranged to act on a stopper inside said medicament container; a driving means arranged to interact with said plunger rod; wherein said device further comprises an operation member transversally protruding through an elongated opening on the longitudinal surface of the elongated housing and interactively connected to the driving means for both setting and actuating the delivery of a dose of medicament.

According to a further aspect of the invention, said driving means comprises a first elongated plate parallelly arranged in relation to the plunger rod and comprising the operation member; a second elongated plate parallelly arranged in relation to the plunger rod and positioned generally opposite to the first elongated plate; a lock member operatively connected to the plunger rod by first one-direction locking means such that the plunger rod can be linearly and proximally displaced but locked against a distally displacement; and a linear movable driver operatively connected to both the first and the second elongated plates by gear means, and also operatively connected to the plunger rod by second one-direction locking means such that when said operation member is manually and distally displaced a certain distance corresponding to a set dose, said driver is also distally displaced in relation to said plunger rod and when said operation member is manually and proximally displaced, both the plunger rod and the driver which are locked to each other by the second one-direction locking means are also proximally displaced.

According to a another aspect of the invention, said the first and the second one-direction locking means locking means are at least one flexible ratchet arm having a tooth-like protrusion and a longitudinal extending ratchet on the longitudinal surface of the plunger rod arranged to interact with each other.

According to yet a further aspect of the invention, said the first elongated plate is longitudinally slidable on a guiding means on the inner surface of the elongated housing and the second elongated plate is fixedly attached to the inner surface of the elongated housing.

According to yet a further aspect of the invention, said the gear means are at least one first cog-wheel rotatably arranged on said driver and at least one longitudinally extending ratchet on each of the longitudinal inner surfaces of the first and the second elongated plates, wherein said at least one first cog-wheel is arranged to interact with each of the longitudinally extending ratchets.

According to a further aspect of the invention, said the first and the second elongated plates are longitudinally slidable on guiding means on the inner surface of the elongated housing.

According to another aspect of the invention, said the gear means are a first cog-wheel rotatably arranged on said driver, a second cog-wheel rotatably arranged on said lock member, a third cog-wheel coaxially and fixedly arranged to the second cog-wheel and also rotatably arranged on said lock member, a first longitudinally extending ratchet on the longitudinal inner surface of the first elongated plate, and a second and a third longitudinally extending ratchets on the longitudinal inner surfaces of the second elongated plate; wherein said first cog-wheel is arranged to interact with the first longitudinally extending ratchet and with the second longitudinally extending ratchet, wherein said second cog-wheel is arranged to interact with the first longitudinally extending ratchet, and wherein said third cog-wheel is arranged to interact with the third longitudinally extending ratchet.

According to yet a further aspect of the invention, an alternative manually activation member is connected or integrally build to the first elongated plate, and wherein the distal end of the alternative activation member is arranged to protrude through the distal end of the housing when the operation member is manually and distally displaced a certain distance corresponding to a set dose.

According to yet a further aspect of the invention, a dose limiting means is adapted to be releasibly attached on the elongated opening on the longitudinal surface of the elongated housing.

There are a number of advantages with the present invention. The use of a linearly operable dose setting member provides an intuitive and easy to handle solution in contrast to the turning of a dose setting knob. It is generally easier for users with reduced dexterity and hand precision to make a sliding movement than to make a turning movement.

Also, in order to further facilitate the handling, a gear is provided, which reduces the force needed for tensioning the spring force means and setting a dose.

The dual function of the dose setting member, i.e. dose setting and tensioning the spring, means that the device can be stored for long periods without the risk of material deterioration and subsequent malfunctioning due to loaded springs.

The use of a plunger rod arranged with ratchet and dose setting means and release mechanism cooperating with the ratchet provides a device with a lot of functionality but with few components.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
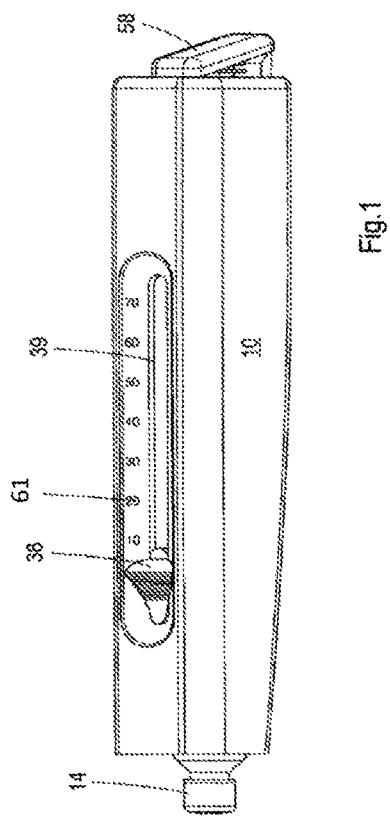
FIG. 1 shows a side view of a medicament delivery device according to a first embodiment of the present invention.
Figure 2:
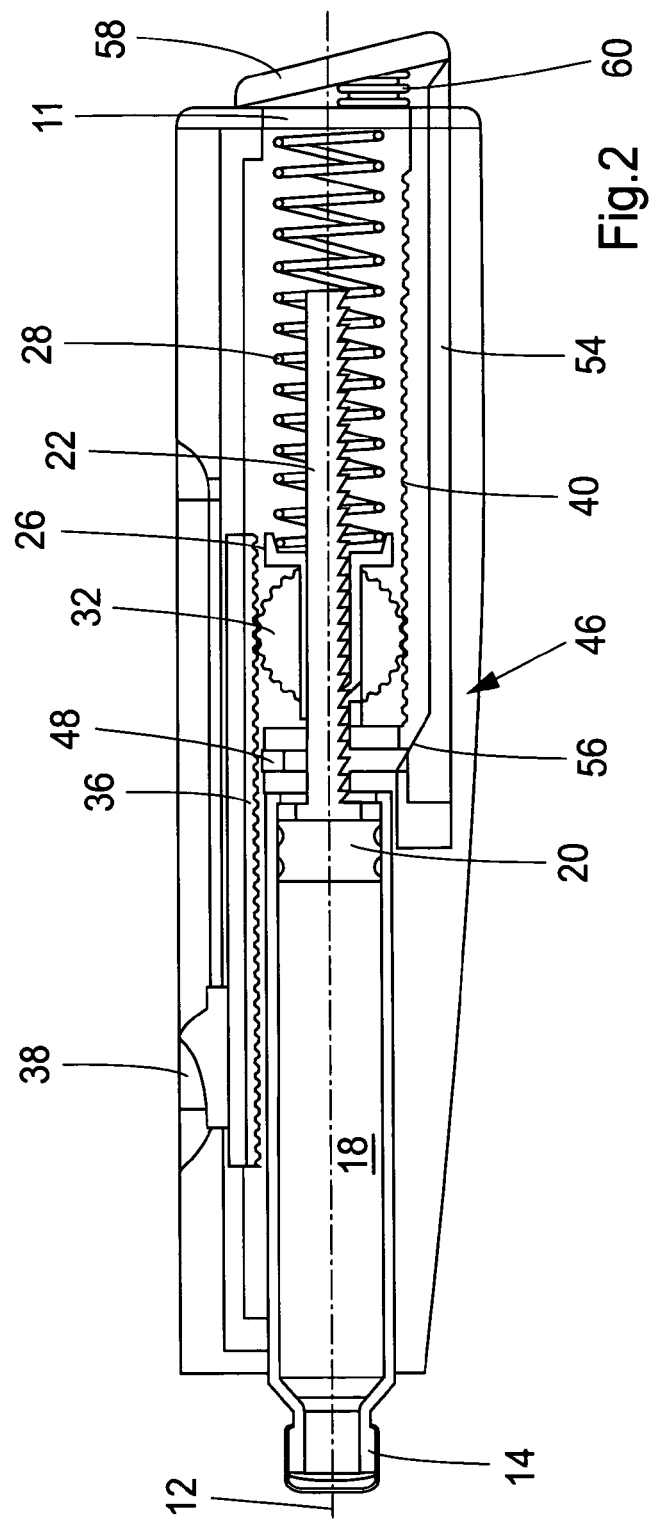
FIG. 2 shows a cross-sectional side view of the device of FIG. 1, FIGS. 3-5 show detailed views of a driving means of the device of FIG. 1.

In the present application, when the term "distal part/end" is used, this refers to the part/end of the medicament delivery device, or the parts/ends of the members thereof, which under use of the medicament delivery device is located the furthest away from the medicament delivery site of the patient.

Correspondingly, when the term "proximal part/end" is used, this refers to the part/end of the medicament delivery device, or the parts/ends of the members thereof, which under use of the injection device is located closest to the medicament delivery site of the patient.

The present invention relates to a medicament delivery device comprising an elongated housing 10, 10' having opposite distal and proximal ends, a medicament container 18; 18' arranged inside said housing, a medicament delivery member 16; 16' attachable to said medicament container; a plunger rod 22; 22' arranged to act on a stopper 20; 20' inside said medicament container; and driving means arranged to interact with said plunger rod; wherein said device further comprises an operation member 38; 38' transversally protruding through an elongated opening 39; 39' on the longitudinal surface of the elongated housing and interactively connected to the driving means for both setting and actuating the delivery of a dose of medicament.

The driving means comprises a first elongated plate 36; 36' parallelly arranged in relation to the plunger rod and comprising the operation member 38; 38'; a second elongated plate 40; 40' parallelly arranged in relation to the plunger rod and positioned generally opposite to the first elongated plate; a lock member 48; 48' operatively connected to the plunger rod by first one-direction locking means such that the plunger rod can be linearly and proximally displaced but locked against a distally displacement; and a linear movable driver 24; 24' operatively connected to both the first and the second elongated plates by gear means, and also operatively connected to the plunger rod by second one-direction locking means such that when said operation member is manually and distally displaced a certain distance corresponding to a set dose, said driver is also distally displaced in relation to said plunger rod and when said operation member is manually and proximally displaced, both the plunger rod and the driver which are locked to each other by the second one-direction locking means are also proximally displaced.

A first embodiment of the present invention is shown in the drawings 1-10. The medicament delivery device comprises the elongated housing 10 having opposite distal and proximal ends and extending in a longitudinal direction 12, FIG. 1. Inside the housing, the medicament container 18 is arranged. The proximal end of the housing, to the left in the drawings, is arranged with an attachment means as e.g. a neck 14 onto which the medicament delivery member 16, such as a needle may be attached to the medicament container. The attachment means could comprise threads, bayonet fittings, snap-on fittings and the like. Other medicament delivery members could comprise nozzles, mouthpieces and the like. The medicament container 18 may be arranged, with a proximal end adapted to fit into the neck 14. The medicament container 18 has a generally tubular shape and is arranged with an axially slidable and sealingly arranged stopper 20, where the container and stopper define a closed chamber containing a volume of medicament.

The elongated plunger rod 22 having a proximal end and distal end is further arranged movable inside said housing generally in the longitudinal direction and is arranged to be in contact with its proximal end with said stopper 20. The plunger rod 22 further passes through opening 24a in the linear movable driver 24, arranged slidable in the longitudinal direction, hereafter named driver.

The first elongated plate 36 is parallelly arranged in relation to the plunger rod and comprises the operation member 38 as e.g. a button transversally protruding through the elongated opening 39 on the longitudinal surface of the elongated housing for setting and/or actuating the delivery of a dose of medicament.

The second elongated plate 40 being parallelly arranged in relation to the plunger rod and positioned generally opposite to the first elongated plate 36.

The lock member 48 being operatively connected to the plunger rod by first one-direction locking means such that the plunger rod can be linearly and proximally displaced but locked against a distally displacement. The lock member is positioned generally transversal to the longitudinal direction of the device and is arranged with a central opening 50 through which the plunger rod extends. The first one-direction locking means are arranged on the inner surface of the central opening 50. Further, the lock member is either a separate component connected to the housing or integrally built to the housing.

The linear movable driver 24 is operatively connected to both the first and the second elongated plates by gear means, and is also operatively connected to the plunger rod by second one-direction locking means such that when said operation member is manually and distally displaced a certain distance corresponding to a set dose, said driver is also distally displaced in relation to said plunger rod and when said operation member is manually and proximally displaced, both the plunger rod and the driver which are locked to each other by the second one-direction locking means are also proximally displaced.

The first and the second one-direction locking means locking means are at least one flexible ratchet arm 44 having a tooth-like protrusion 52, and a longitudinal extending ratchet 42 on the longitudinal surface of the plunger rod, wherein the tooth-like protrusion 52 of the at least one ratchet arm 44 and the longitudinal extending ratchet 42 of the first one-direction locking means are formed such that the plunger rod can be linearly and proximally displaced but locked against a distally displacement when the plunger rod is linearly displaced through the central opening 50 of the lock member 48, and wherein the tooth-like protrusion 52 of the at least one ratchet arm 44 and the longitudinal extending ratchet 42 of the second one-direction locking means are formed such that the driver can be linearly and distally displaced over the plunger rod when the plunger rod is held locked against distal displacement by the second one-direction locking means and locked to the plunger rod when the driver is linearly and proximally displaced.

In the first embodiment, the first elongated plate 36 is longitudinally slidable on a guiding means on the inner surface of the elongated housing and the second elongated plate 40 is fixedly attached to the inner surface of the elongated housing. An alternative is to have the second elongated plate integral with the housing.

Also in the first embodiment, the gear means are at least one first cog-wheel 32 rotatably arranged on side 24b of said driver, and at least one longitudinally extending ratchet 34, 41 on each of the longitudinal inner surfaces of the first and the second elongated plates, wherein said at least one first cogwheel 32 has teeth 32a arranged to interact with each of the longitudinally extending ratchet 34, 41.

Figure 3:
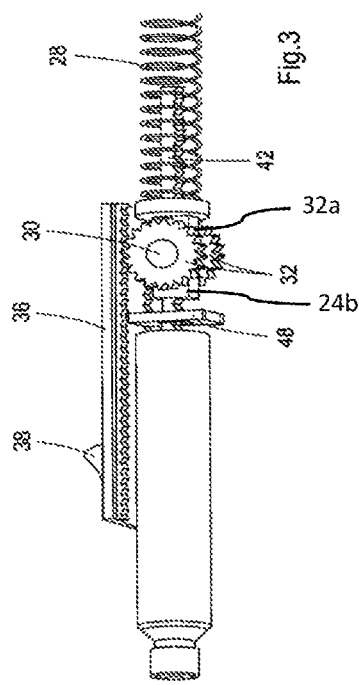
Figure 4:
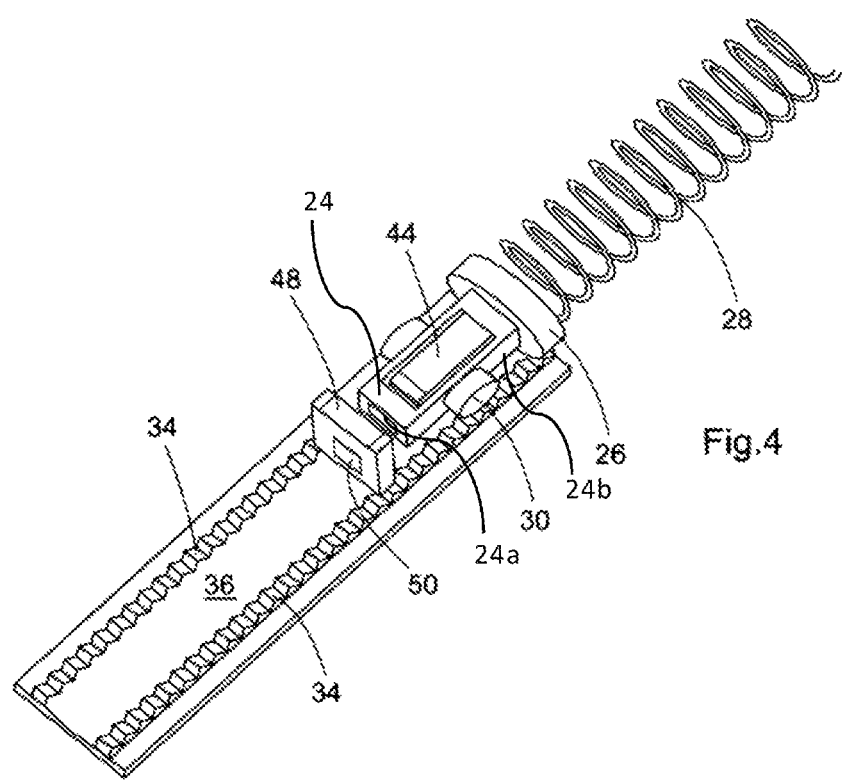
Figure 5:
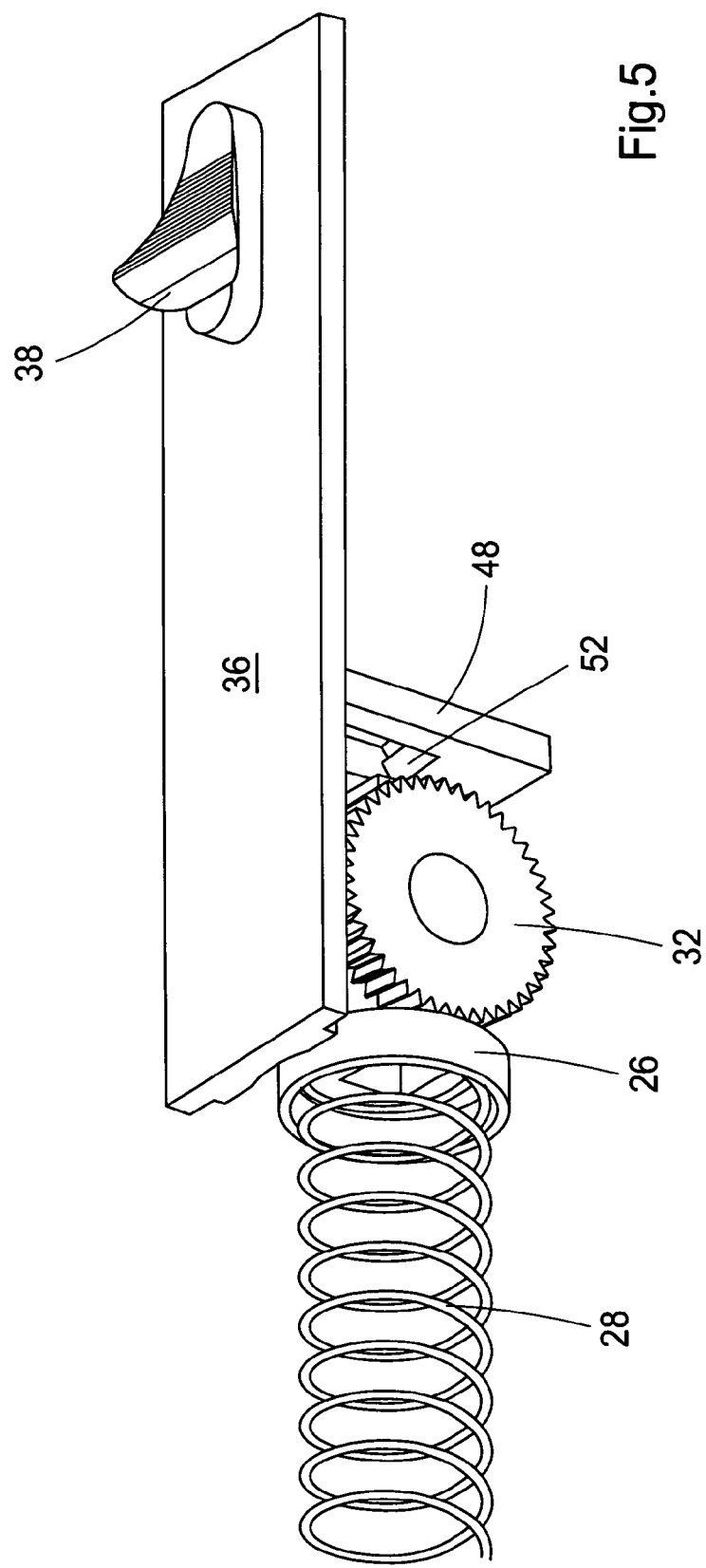
Figure 6:
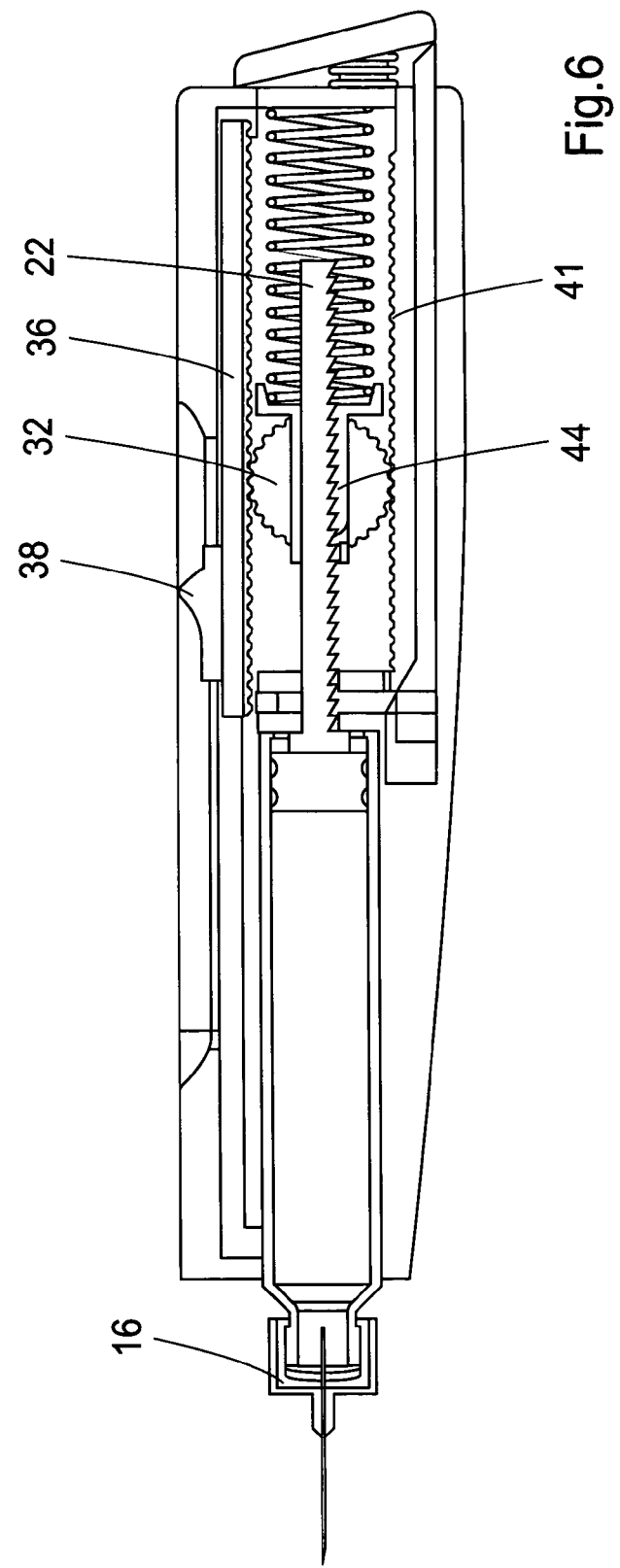
FIG. 6 shows a cross-sectional view according to FIG. 2 when a dose has been set.
Figure 7:
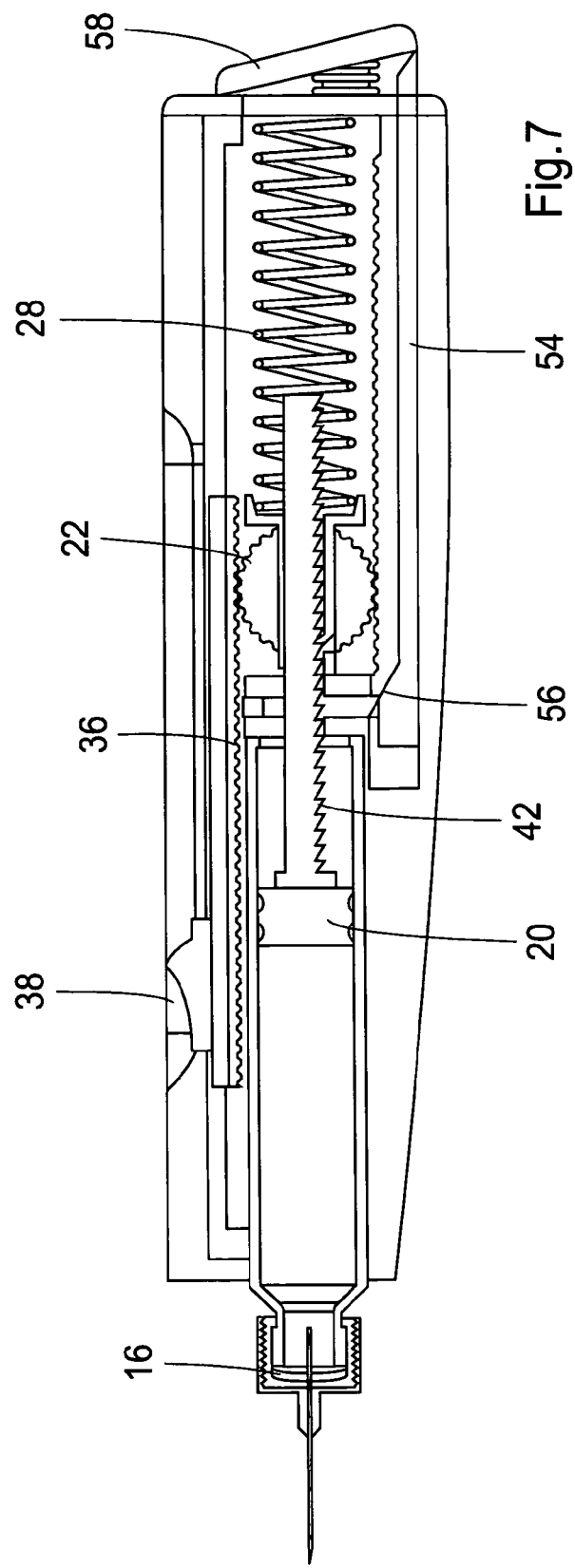
FIG. 7 shows a cross-sectional view according to FIG. 2 when a dose has been delivered.

As shown in FIG. 3, the driver 24 may be arranged with two shafts 30 arranged on opposite sides of the driver and directed generally transversal to the longitudinal direction of the device. On each shaft a first cog-wheel 32 is rotatably arranged. Each first cog-wheel 32 cooperates with a corresponding longitudinally extending ratchet 34 arranged on a surface of the first elongated plate 36, and with a corresponding longitudinally extending ratchet 41 arranged on a surface of the second elongated plate 40.

As shown in the FIGS. 2-8, the driver 24 may further be arranged with an annularly arranged surface at its distal end, which surface is provided with edges, thus forming a cup 26. A spring force means 28 may be arranged between said cup 26 and a distal wall surface of the housing 10. The spring force means is arranged to act on said plunger rod 22 for forcing said plunger rod 22 against said stopper 20 for expelling medicament through said medicament delivery member 16. The spring force means 28 can comprise a number of different force means, such as leaf springs, volute springs, pneumatic or hydraulic springs or any other type of non-electric power source suitable for the intended use according to the present invention. The gear means are arranged to interact with each other for reducing the force needed for the tensioning of said spring force means 28. Further, a manually operated release mechanism 46 is releasably connected to said plunger rod such that when said release mechanism is engaged to the plunger rod, said plunger rod is in a non-medicament delivery state and when said release mechanism is disengaged from said plunger rod, said plunger rod is in a medicament delivery state. The release mechanism comprises a release rod 54, FIG. 2, extending generally in the longitudinal direction 12 inside the housing and having a proximal end and a distal end. The proximal end of the release rod 54 is positioned adjacent the lock member 48 which is arranged as a transversally movable separate component. The proximal end of the release rod 54 is provided with a ledge 56, which in an initial position is in contact with the lock member such that the protrusion 52 is engaging the ratchet 42 of the plunger rod 22. A spring (not shown) is arranged for urging the lock member 48 against the ledge 56. The distal end of the release rod 54 extends through a distal end wall 11 of the housing and is in contact with a push button 58 pivotally attached to the distal end wall 11 of the housing 10. A spring 60 is arranged between the outer surface of the end wall 11 and the push button 58 for urging the latter in a raised position.

The first embodiment is intended to function as follows. When the device is to be used, a proper medicament delivery member 16 is attached to the neck 14 at the proximal end of the device. In order to deliver a dose of medicament, the device has to be armed. This is done when the plunger rod is in a non-medicament delivery state by sliding the button 38 linearly along the elongated opening 39 such that the button 38 and the plate 36 slide in the longitudinal direction of the device towards the distal end. Due to the connection between the at least one longitudinally extending ratchet 34 of the plate 36 and the at least one first cog-wheel 32, the movement of the plate 36 causes the at least one first cog-wheel 32 to rotate and because of the connection between the at least one first cog-wheel 32 and the at least one longitudinally extending ratchet 41, the driver 24 will be moved in the distal direction of the device while the plunger rod will be held in place by the first one-direction locking means.

The use of cog-wheels acting on longitudinally extending ratchets provides a transmission that reduces the force needed at the same time as the dose setting precision is improved due to the gear ratio.

Further, the movement of the driver 24 causes the spring force means 28 to be compressed and thus tensioned. During the movement of the driver 24 the flexible ratchet arm 44 of the driver 24 slides over the ratchet 42 of the plunger rod 22 since the plunger rod is held in place by the connection between the first one-direction locking means. When the desired dose is set, i.e. the button 38 has been slid to a certain position along the elongated opening, which may be arranged with indicia 61, FIG. 1, such as e.g. dose quantity indications, broken lines or dots along the opening, informing the dose quantity, or if a fixed dose is to be delivered, the button has been slid to the end of the opening, the device is ready for medicament delivery, FIG. 6. The driver is now locked to the plunger rod 22 by the second one-direction locking means such that both can be proximally displaced. When a dose is to be delivered, the proximal end of the device is placed in the proper delivery position, which could be an injection site for an injector, or the mouth for an inhaler. The push button 58 is now pressed against the force of the spring 60 causing the release rod 54 to be pushed in the longitudinal direction towards the proximal end of the device, whereby the ledge 56 of the proximal end of the release rod 54 is moved out of contact with the lock member 48. This is in turn free to slide in the transversal direction due to the force of the spring, whereby the protrusion 52 is moved out of contact with the ratchet 42 of the plunger rod 22, such that the plunger rod is in the medicament delivery state. The plunger rod 22 is now moved in the proximal direction by the force of the spring force means 28 pushing proximally both the driver 24 and the plunger rod 22. The movement of the driver 24 causes the at least one first cog-wheel 32 to rotate, whereby the plate 36 and the operation member 38 are moved back to their original position. The movement of the plunger rod 22 causes the stopper 20 to move towards the proximal end of the device inside the medicament container 18, whereby a dose of medicament is expelled through the medicament delivery member 16. The above described operation may be performed a number of times until the medicament container 18 is empty.

Figure 9:
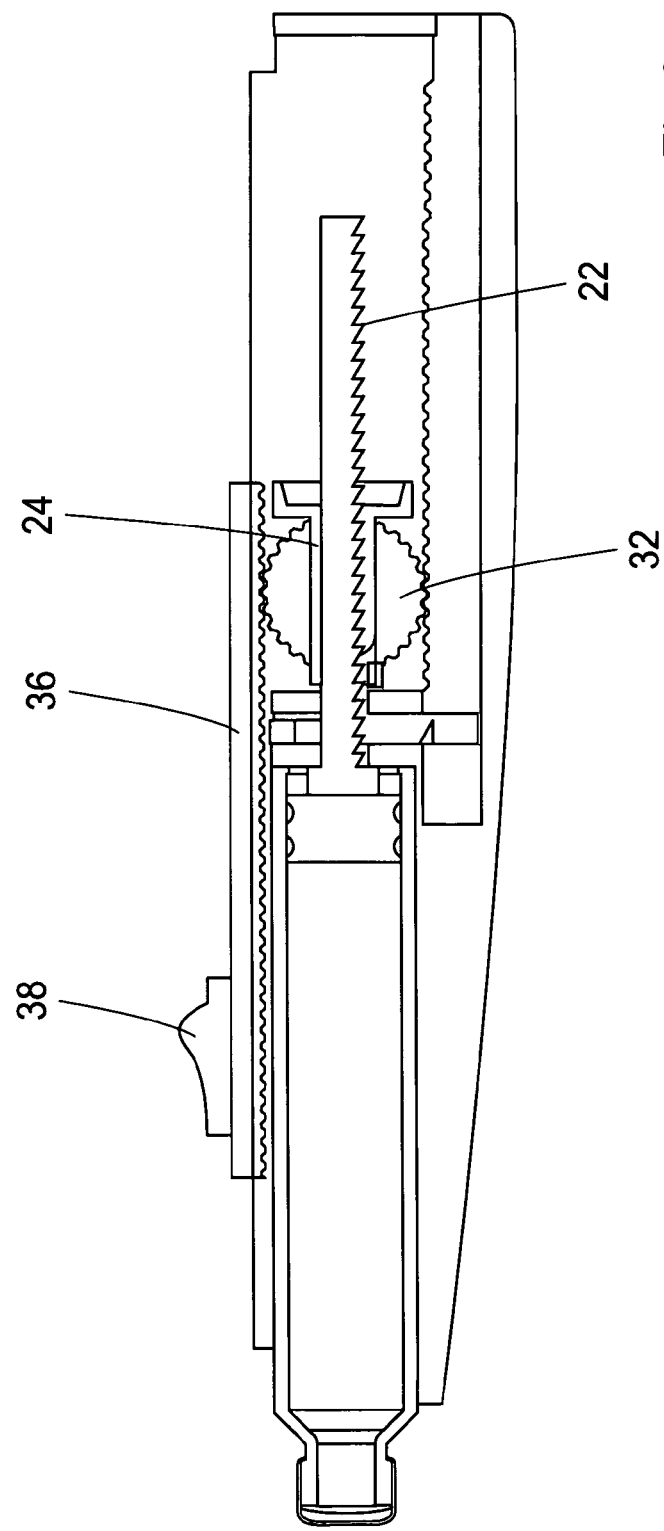
FIG. 9 shows a cross-sectional view of an alternative of the first embodiment of the medicament delivery device according to the invention.

If a cheaper medicament delivery device is to be developed, the delivery operation may be performed manually. FIG. 9 shows one variant where the spring has been removed. When the plunger rod is in the non-medicament delivery state, the driver 24 is then moved manually by sliding the operation member 38 whereby the at least one cog-wheel 32 rotate, in the manner described above, until the desired dose is set. In order to deliver the set dose, the plunger rod is set in the medicament delivery state by manually sliding the operation member 38 back to their initial position, whereby the plunger rod 22 is proximally moved together with the first elongated plate 36 via the driver 24 such that a dose is delivered.

A second embodiment of the present invention is shown in the drawings 11-15. The medicament delivery device comprises an elongated housing 10' having opposite distal and proximal ends and extending in a longitudinal direction. Inside the housing, the medicament container 18' is arranged. The proximal end of the housing, to the left in the drawings, is arranged with an attachment means as e.g. a neck 14' onto which a medicament delivery member, such as a needle may be attached to the medicament container. The attachment means could comprise threads, bayonet fittings, snap-on fittings and the like. Other medicament delivery members could comprise nozzles, mouthpieces and the like. The medicament container 18' may be arranged, with a proximal end adapted to fit into the neck 14'. The medicament container 18' has a generally tubular shape and is arranged with an axially slidable and sealingly arranged stopper 20', where the container and stopper define a closed chamber containing a volume of medicament.

The elongated plunger rod 22' having a proximal end and distal end is further arranged movable inside said housing generally in the longitudinal direction and is arranged to be in contact with its proximal end with said stopper 20'. The plunger rod 22' further passes through the linear movable driver 24', arranged slidable in the longitudinal direction, hereafter named driver.

The first elongated plate 36' is parallelly arranged in relation to the plunger rod and comprises the operation member 38' as e.g. a button transversally protruding through an elongated opening 39' on the longitudinal surface of the elongated housing for setting and/or actuating the delivery of a dose of medicament.

The second elongated plate 40' being parallelly arranged in relation to the plunger rod and positioned generally opposite to the first elongated plate 36'.

The lock member 48' being operatively connected to the plunger rod by first one-direction locking means such that the plunger rod can be linearly and proximally displaced but locked against a distally displacement. The lock member is positioned generally transversal to the longitudinal direction of the device and is arranged with a central opening 50' through which the plunger rod extends. The first one-direction locking means are arranged on the inner surface of the central opening 50'. Further, the lock member is either a separate component connected to the housing or integrally built to the housing.

The linear movable driver 24' is operatively connected to both the first and the second elongated plates by gear means, and is also operatively connected to the plunger rod by second one-direction locking means such that when said operation member is manually and distally displaced a certain distance corresponding to a set dose, said driver is also distally displaced in relation to said plunger rod and when said operation member is manually and proximally displaced, both the plunger rod and the driver which are locked to each other by the second one-direction locking means are also proximally displaced.

The first and the second one-direction locking means locking means are at least one flexible ratchet arm 44' having a tooth-like protrusion 52', and a longitudinal extending ratchet 42' on the longitudinal surface of the plunger rod, wherein the tooth-like protrusion 52' of the at least one ratchet arm 44' and the longitudinal extending ratchet 42' of the first one-direction locking means are formed such that the plunger rod can be linearly and proximally displaced but locked against a distally displacement when the plunger rod is linearly displaced through the lock member 48', and wherein the tooth-like protrusion 52' of the at least one ratchet arm 44' and the longitudinal extending ratchet 42' of the second one-direction locking means are formed such that the driver can be linearly and distally displaced over the plunger rod when the plunger rod is held locked against distal displacement by the second one-direction locking means and locked to the plunger rod when the driver is linearly and proximally displaced.

In the second embodiment, the first and the second elongated plates are longitudinally slidable on guiding means on the inner surface of the elongated housing.

Also in the second embodiment, the gear means are a first cog-wheel 32' rotatably arranged on said driver, a second cog-wheel 31 rotatably arranged on said lock member, a third cog-wheel 33 coaxially and fixedly arranged to the second cog-wheel 31 and also rotatably arranged on said lock member, a first longitudinally extending ratchet 34' on the longitudinal inner surface of the first elongated plate 36', and a second 41' and a third 43 longitudinally extending ratchets on the longitudinal inner surfaces of the second elongated plate 40'; wherein said first cog-wheel 32' is arranged to interact with the first longitudinally extending ratchet 34' and with the second longitudinally extending ratchet 41', wherein said second cog-wheel 31 is arranged to interact with the first longitudinally extending ratchet 34', and wherein said third cog-wheel is arranged to interact with the third longitudinally extending ratchet 43.

Figure 13:
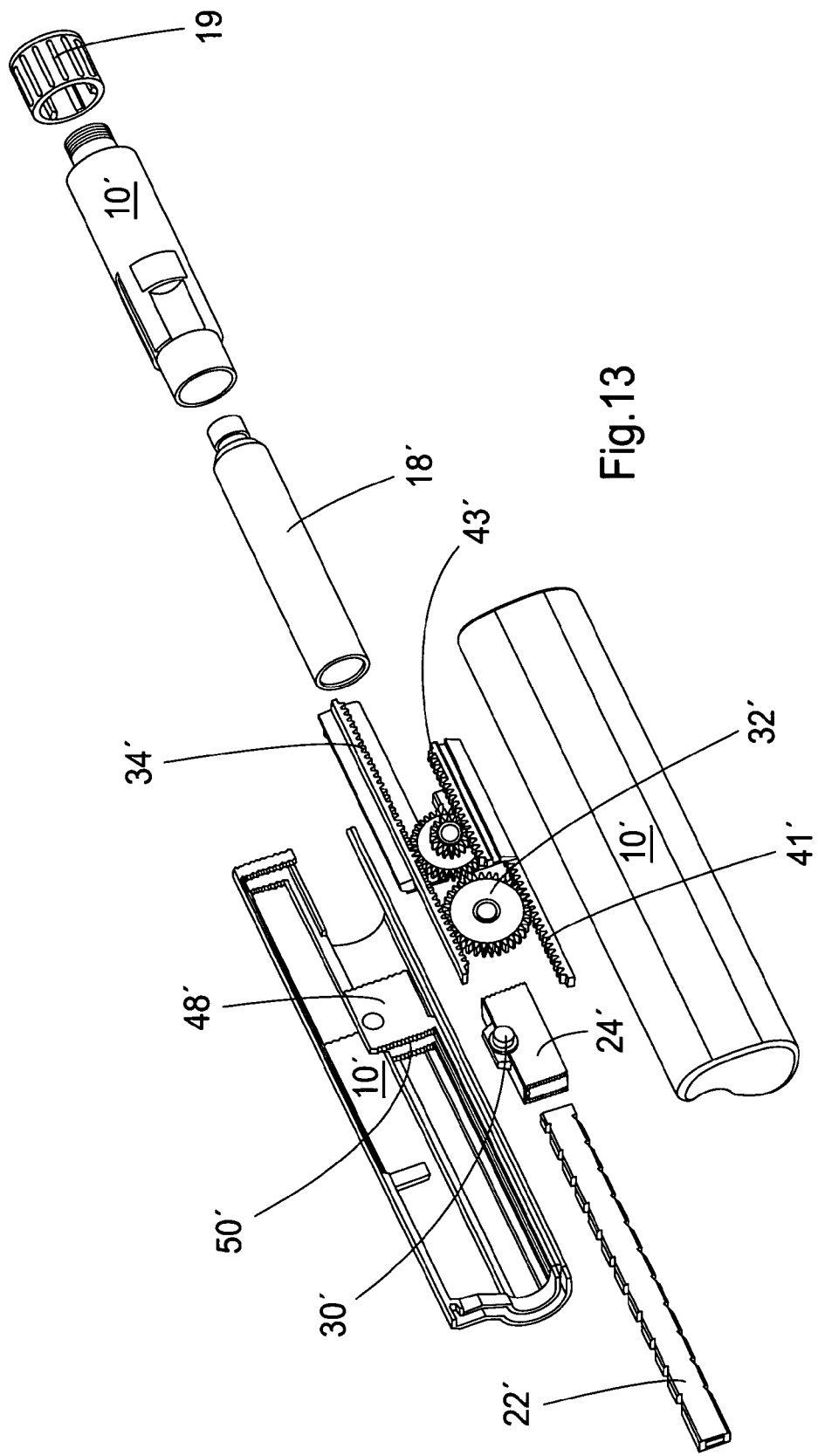
FIG. 13 shows a second exploded perspective view of the device of FIG. 11.
Figure 14:
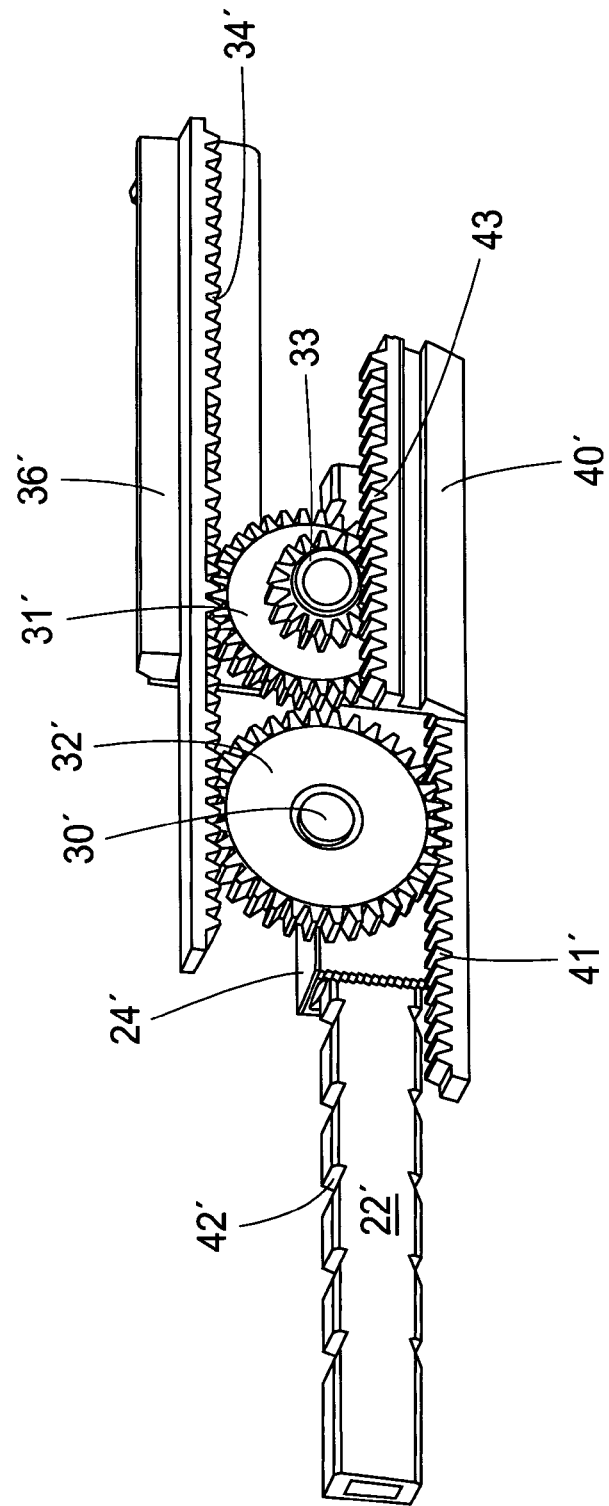
FIG. 14 shows a detailed view of a driving means of the device of FIG. 11.
Figure 15:
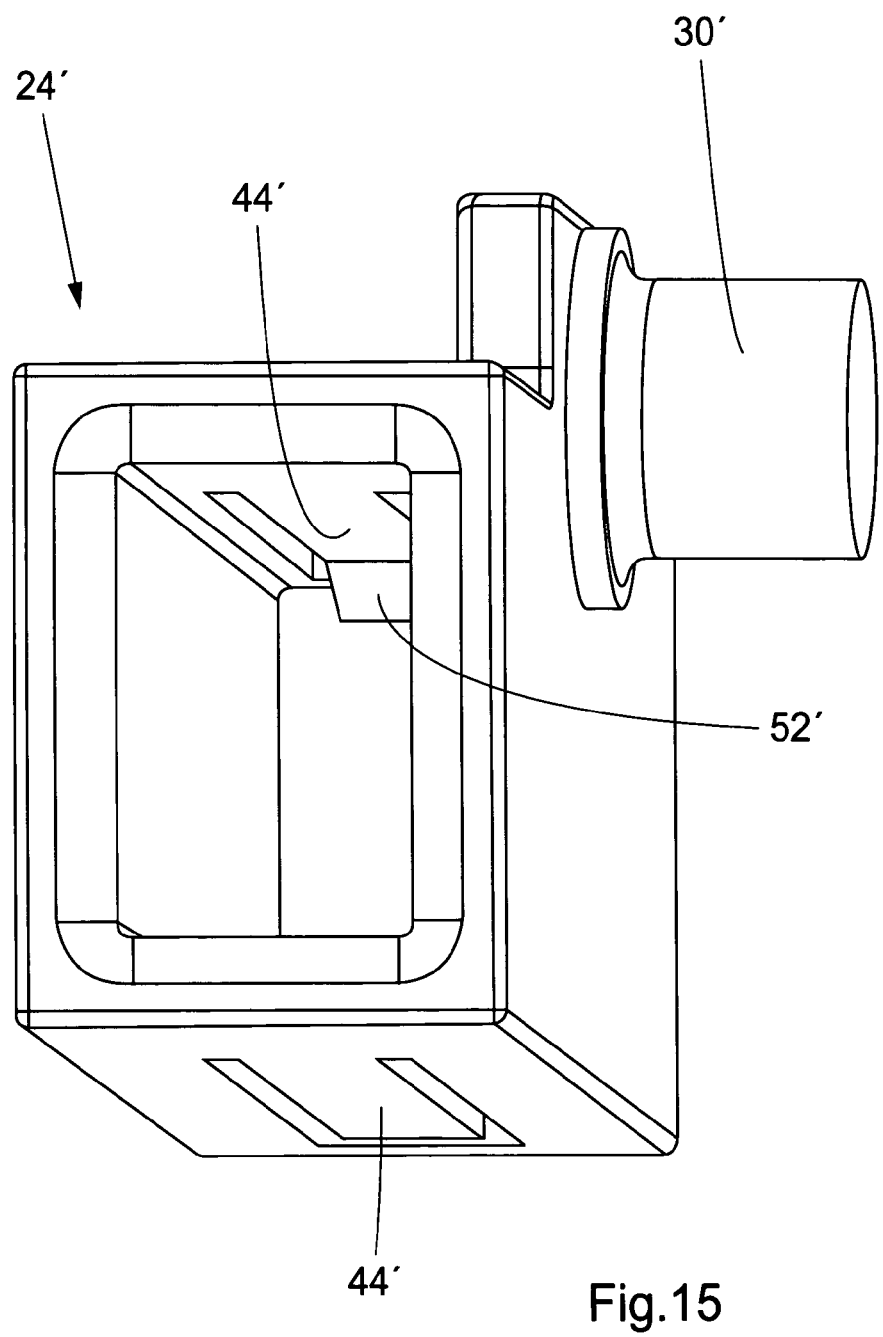
FIG. 15 shows a detailed view of a driver of the device of FIG. 11.

As shown in FIG. 13, the driver 24 may be arranged with a first shaft 30' directed generally transversal to the longitudinal direction of the device. On the first shaft, the first cog-wheel 32' is rotatably arranged. Further, the diameter of the third cog-wheel 33 is smaller than the diameter of the second cog-wheel 31 as well as the diameter of the first cog-wheel 32'.

Further, the lock member 48' may be arranged with a second shaft directed generally transversal to the longitudinal direction of the device. On the second shaft, the second cog-wheel 32' and the third cog-wheel 33 are rotatably arranged.

The second embodiment is intended to function as follows. When the device is to be used, a protective cap 19 is removed and a proper medicament delivery member is attached to the neck 14' at the proximal end of the device. In order to deliver a dose of medicament, the device has to be armed. This is done by sliding the operation member 38' linearly along the elongated opening 39' such that the operation member 38' and the first elongated plate 36' slide in the longitudinal direction of the device towards the distal end.

This causes the first cog-wheel 32' and the second cog-wheel 31 to rotate due to the engagement between the first and the second cog-wheels with the first longitudinally extending ratchet 34'. The rotation of the second cog-wheel 31 causes the third wheel 33 to rotate and thereby the second elongated plate 40' to slide in the proximal direction because the connection between the third wheel 33 and the third longitudinally extending ratchet 43, and because the second and the third cog-wheels are fixed in the housing through the lock member 48'. The rotation of the first cog-wheel 32' causes the driver 24' to be moved in the distal direction while the plunger rod is held in place by the first one-direction locking means.

Because the third cog-wheel 33 has a smaller diameter than the second cog-wheel 31, the linear distance that the second elongated plate 40' is moved is shorter than the linear distance that the operation member 38' and its first elongated plate 36' is moved. In turn, this causes the driver 24' to move a shorter linear distance because of the attachment of the first cog-wheel to the driver and because of the engagement of the first cog-wheel with the first elongated plate 36. I.e. a longer linear movement of the operation member when setting a dose provides a shorter movement of the driver along the plunger rod, which enables more accuracy in setting a certain dose. By the above it is to be understood that changing of the diameter relations between the second and third cog-wheel, the transmission can be changed to the preferred situation. It is also to be understood that number of teeth of the second and third cog-wheels may be altered in order to obtain the function according to the invention.

The use of cog-wheels acting on longitudinally extending ratchets provides a transmission that reduces the force needed at the same time as the dose setting precision is improved due to the gear ratio.

When the desired dose is set, i.e. the operation member 38' has been slid to a certain position along the elongated opening, which may be arranged with indicia 61, such as e.g. dose quantity indications, broken lines or dots along the opening, informing the dose quantity, or if a fixed dose is to be delivered, the operation member has been slid to the end of the opening, the device is ready for medicament delivery. The driver 24' is now locked to the plunger rod 22' by the second one-direction locking means such that both can be proximally displaced.

When the desired dose is to be delivered, the proximal end of the device is placed in the proper delivery position, which could be an injection site for an injector, or the mouth for an inhaler. By manually and proximally sliding the operation member 38', the first elongated plate 36' is moved back to their initial position, whereby the first cog-wheel 32' is rotated in the opposite direction as described earlier. The rotation of the first cog-wheel 32' now causes the second elongated plate 40' to move in the distal direction. This in turn causes also the driver to be moved in the proximal direction. Since the driver 24' is locked to the plunger rod 22' by the second one-direction locking means, the plunger rod is also forced in the proximal direction. Thereby the stopper is pushed in the proximal direction and the dose of medicament is expelled through the medicament delivery member. By the relation between the diameters of the second and third cog-wheel, the force required by the user in order to expel a dose of medicament is reduced. The above described operation may be performed a number of times until the medicament container 18 is empty.

It is to be understood that the embodiments described above may be modified depending on customer requirements and user preferences. For example, the release button may be placed in other positions on the device, such as on the side of the housing and may be arranged pivoting, or arranged to be depressed or slid, just to mention a few.

Figure 10:
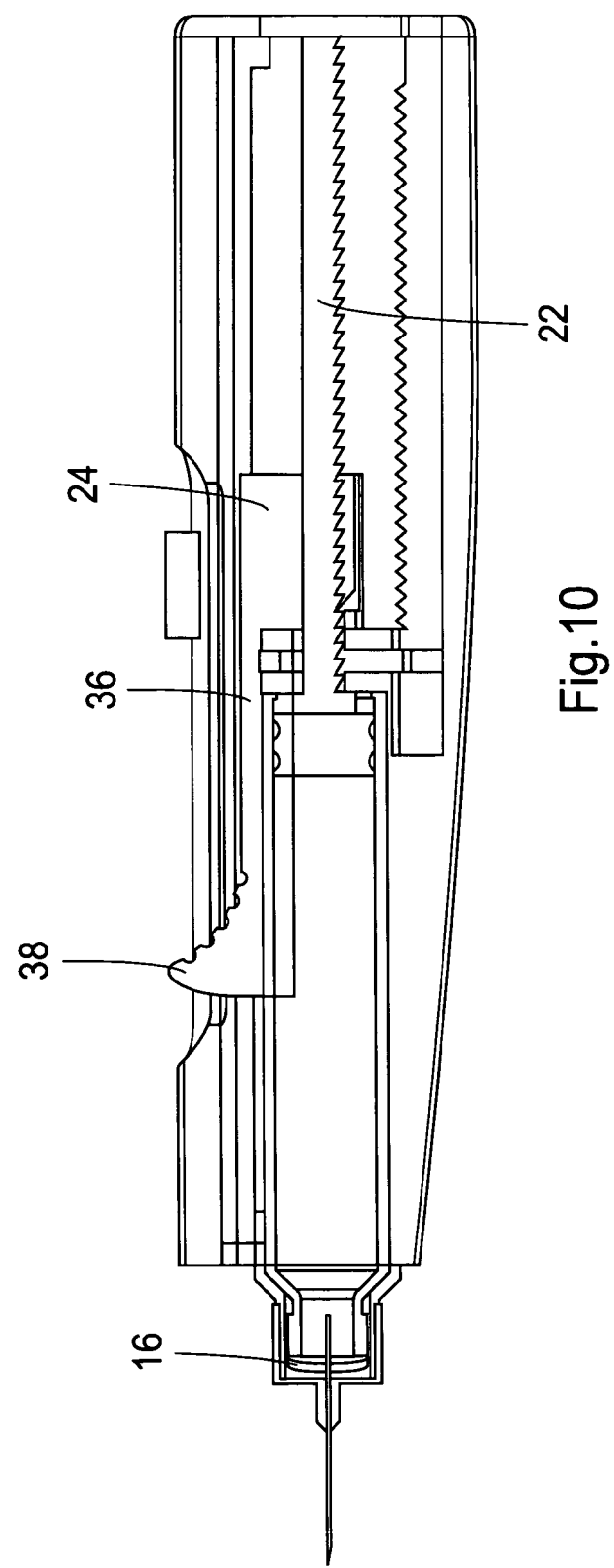
FIG. 10 shows a cross-sectional view of a further alternative of the first embodiment of the medicament delivery device according to the invention.
Figure 11:
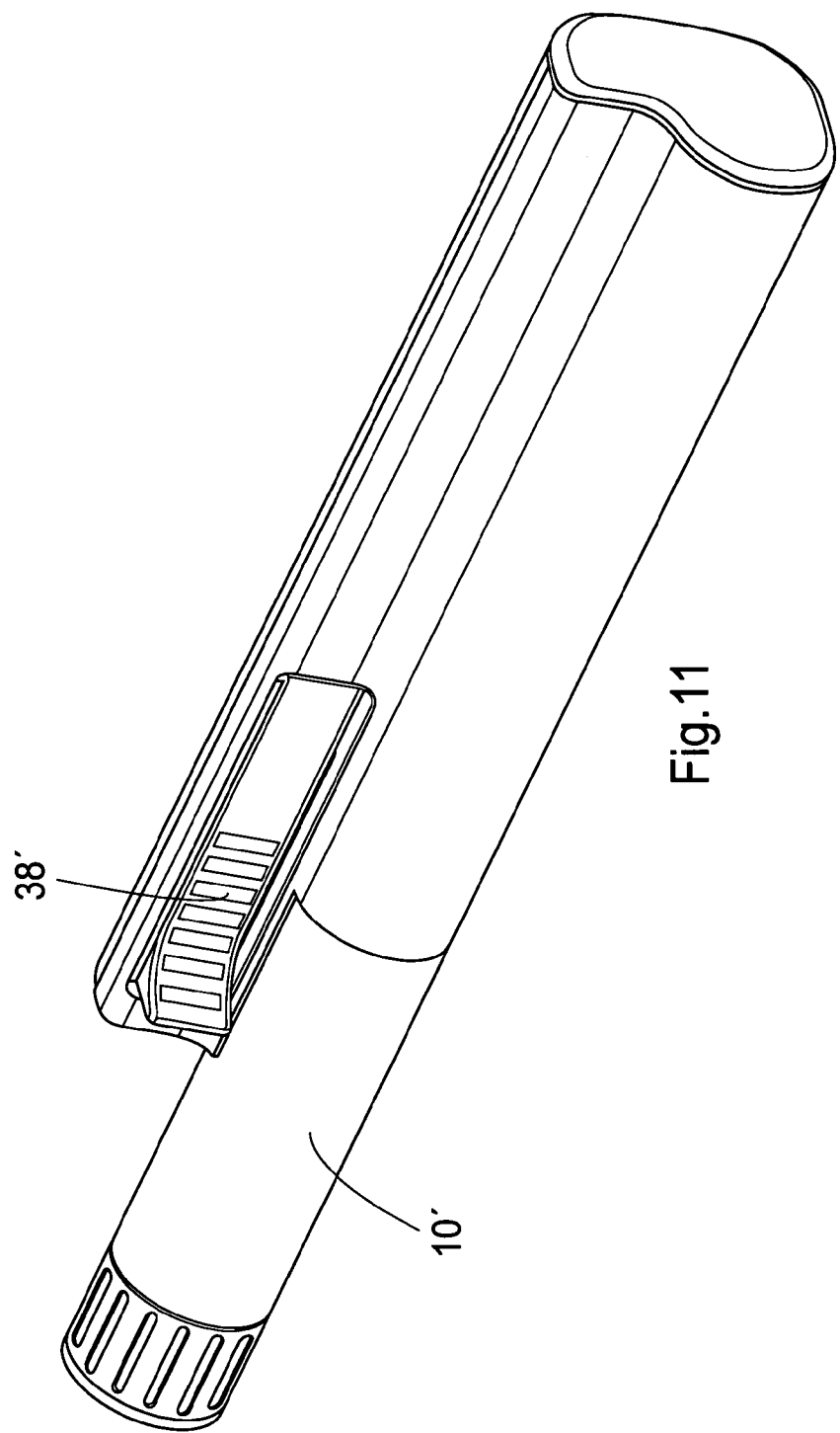
FIG. 11 shows a perspective view of a medicament delivery device according to a second embodiment of the present invention.
Figure 12:
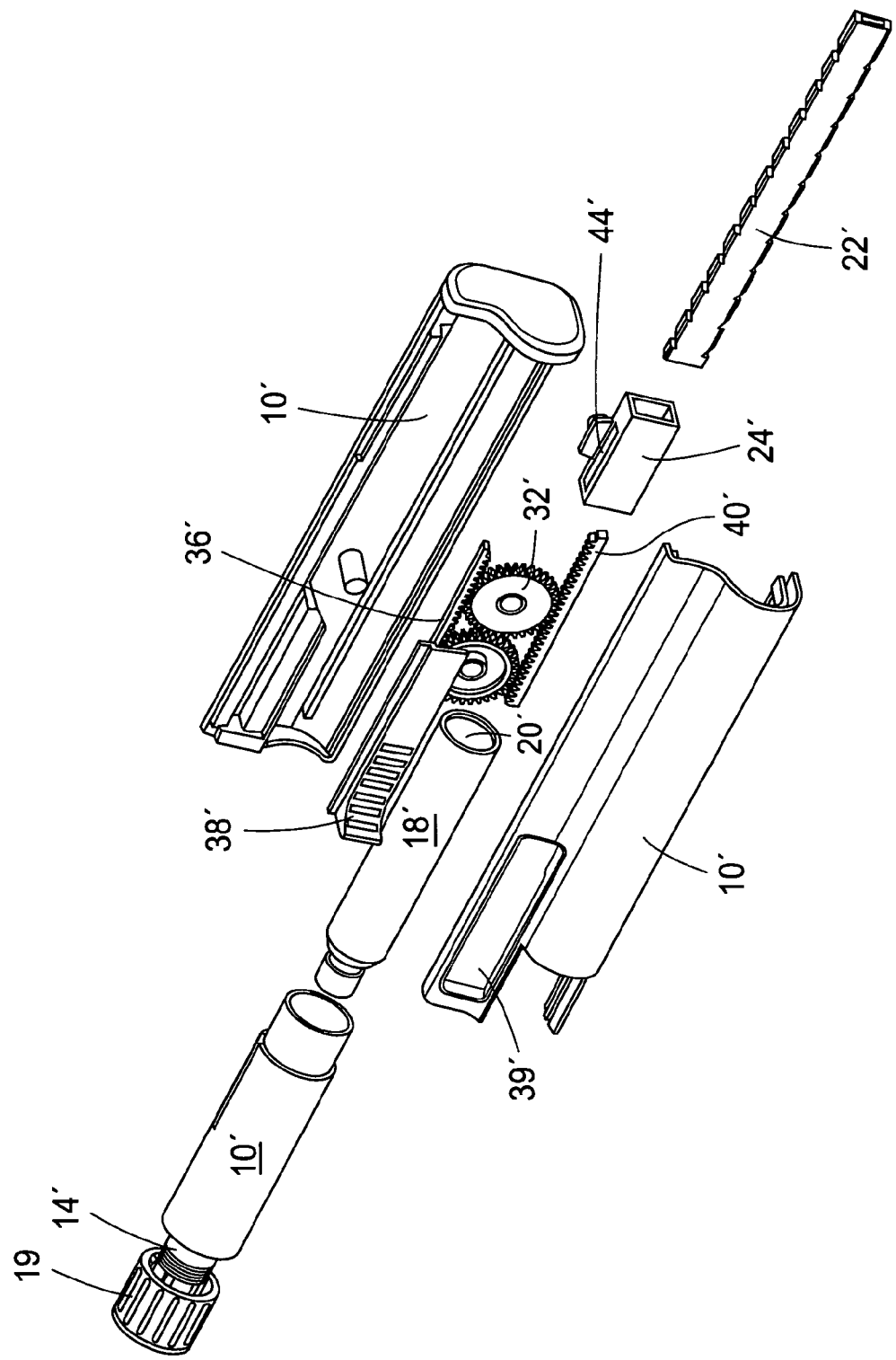
FIG. 12 shows a first exploded perspective view of the device of FIG. 11.

Another example is to have an alternative manually activation member (not shown) connected or integrally build to the first elongated plate 36; 36', as shown in FIG. 10, wherein the distal end of the alternative activation member is arranged to protrude through the distal end of the housing (not shown) when the operation member 38; 38' is manually and distally displaced a certain distance corresponding to a set dose. When the set dose is to be delivered, the alternative manually activation member is manually and proximally pushed, such that the first elongated plate 36; 36', the driver 24; 24' and the plunger rod 22; 22' are also proximally displaced by the gear means, in the manner described above.

Figure 8:
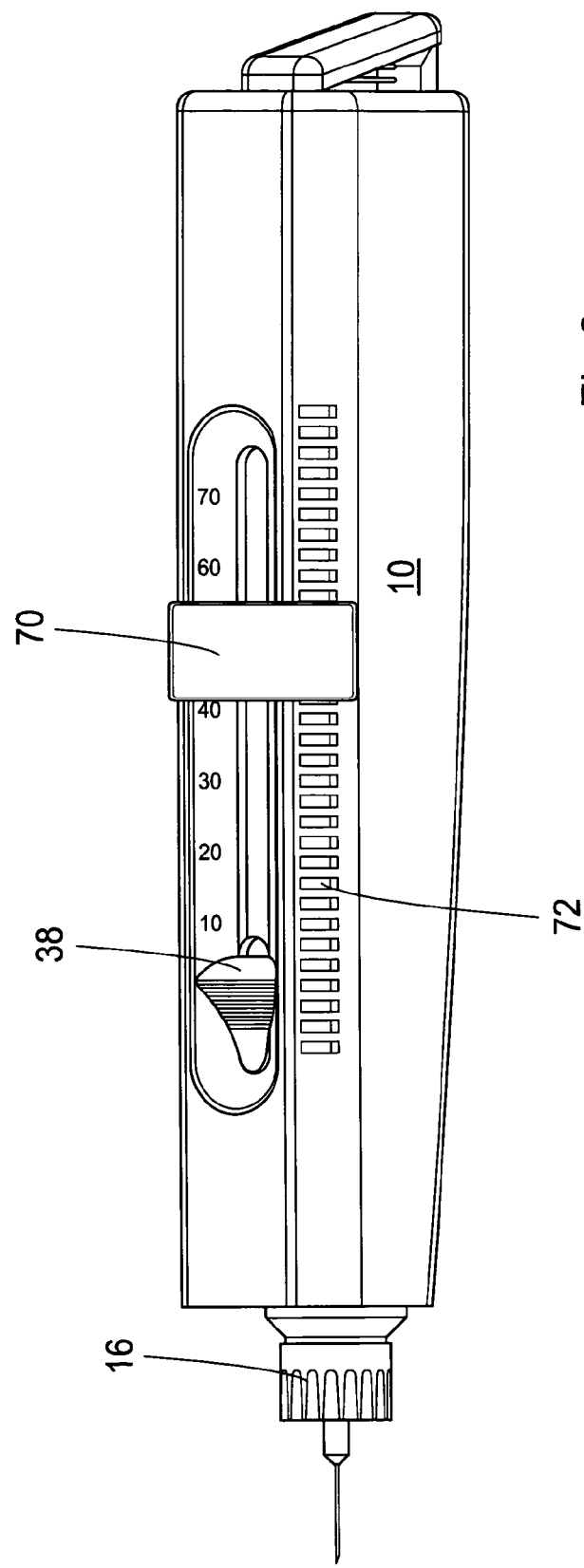
FIG. 8 shows a side view of the device according to FIG. 1 with a dose limiting feature.

Further, as shown in FIG. 8, the device could be arranged with a dose limiting means 70 adapted to be releasably attached on the elongated opening 39; 39' on the longitudinal surface of the elongated housing. The dose limiting means may comprise a clip or the like that is releasibly attached via recesses 72 beside the elongated opening 39; 39' on the longitudinal surface of the elongated housing that can accommodate corresponding protrusions on the clip. In this respect it is to be understood that many different types of fastening means could be utilised. The clip prevents the operation member 38; 38' to be slid beyond its position.

It is to be understood that the embodiments described above and shown in the drawings only are to be regarded as non-limiting examples of the invention and that it may be modified in many ways within the scope of the patent claims.

The invention claimed is:

1. A medicament delivery device, comprising:
   an elongated housing having opposite distal and proximal ends;
   a medicament container arranged inside the housing;
   a medicament delivery member arranged for attachment to the medicament container;
   a plunger rod arranged to act on a stopper inside the medicament container;
   an operation member transversally protruding through an elongated opening on a longitudinal surface of the elongated housing and interactively connected to a linear moveable driver having a longitudinal axis defined by the distal and proximal ends of the elongated housing, the operation member configured for setting a dose of medicament; and
   a first elongated plate arranged in parallel to the plunger rod, directly attached to and axially slidable with the operation member, and having a row of longitudinally extending ratchet teeth;
   a second elongated plate arranged in parallel to the plunger rod, is fixedly attached to the elongated housing having a row of longitudinally extending ratchet teeth, and positioned generally opposite to the first elongated plate; and
   a first one-direction locking device axially fixed to the housing, transversally moveable relative to the longitudinal axis, and releasably connected to the plunger rod, such that the plunger rod is linearly and proximally displaceable but is locked against distal displacement,
   where the linear movable driver comprises an opening, a side parallel to a plane along the longitudinal axis, and a circular shaft directly connected to the side and wherein the shaft extends outwardly from the side laterally and transverse to the longitudinal axis, where the plunger rod passes through the opening and at least one first circular cog-wheel having a central bore that is mounted directly on the shaft such that it rotates relative to the shaft, where the at least first circular cog-wheel has a continuous set of teeth that are directly connected simultaneously to both the rows of longitudinally extending ratchet teeth on the first and the second elongated plates, and where the linear moveable driver is also operatively connected and rotationally fixed relative to the plunger rod during dose setting and during dose delivery by a second one-direction locking device, such that when the operation member is manually and distally displaced a certain distance corresponding to a set dose, the linear movable driver is also distally displaced in relation to the plunger rod, and when the operation member is proximally displaced, both the plunger rod and the linear movable driver, which are directly locked to each other by the second one-direction locking device, are also proximally displaced.

2. The medicament delivery device of claim 1, wherein the second one-direction locking device include at least one tooth-like protrusion that engages a longitudinally extending ratchet on a longitudinal surface of the plunger rod.

3. The medicament delivery device of claim 2, wherein the first elongated plate is longitudinally slidable on an inner surface of the elongated housing, and the second elongated plate is fixedly attached to the inner surface of the elongated housing.

4. The medicament delivery device of claim 3, wherein each of the first and the second elongated plates having a longitudinal inner surface, wherein each of the longitudinal inner surfaces of the first and second elongated plates has a longitudinally extending ratchet; and the at least one first circular cog-wheel is arranged to interact with the one of the longitudinally extending ratchets.

5. The medicament delivery device of claim 1, further comprising an adjustable dose limiting feature releasably attached on the elongated opening on the longitudinal surface of the elongated housing and configured to limit a linear sliding movement of the operation member to a plurality of predetermined positions along the elongated opening on the longitudinal surface of the elongated housing.

6. The medicament delivery device of claim 1, further comprising a spring operatively connected to the linear movable driver and the elongated housing, where the spring forces the plunger rod against the stopper inside the medicament container.

7. The medicament delivery device of claim 6, further comprising a push button configured to release spring force in a proximal direction when the spring is biased after a dose is set.

* * * * *